(12) United States Patent
Sullivan et al.

(10) Patent No.: US 9,376,722 B2
(45) Date of Patent: Jun. 28, 2016

(54) ORAL CARE METHODS AND SYSTEMS

(75) Inventors: Richard Scott Sullivan, Atlantic Highlands, NJ (US); Yanan Hu, San Jose, CA (US); Laurence Du-Thumm, Princeton, NJ (US); Stacey Lavender, Chesterfield, NJ (US); Ralph Peter Santarpia, III, Edison, NJ (US); Zhiqiang Liu, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 380 days.

(21) Appl. No.: 12/866,614

(22) PCT Filed: Feb. 6, 2009

(86) PCT No.: PCT/US2009/033287
§ 371 (c)(1),
(2), (4) Date: Nov. 15, 2010

(87) PCT Pub. No.: WO2009/100262
PCT Pub. Date: Aug. 13, 2009

(65) Prior Publication Data
US 2011/0085990 A1   Apr. 14, 2011

Related U.S. Application Data

(60) Provisional application No. 61/027,437, filed on Feb. 9, 2008, provisional application No. 61/027,442, filed on Feb. 9, 2008, provisional application No. 61/027,420, filed on Feb. 8, 2008, provisional application No. 61/027,431, filed on Feb. 8, 2008, provisional application No. 61/027,432, filed on Feb. 8, 2008.

(51) Int. Cl.
*G01N 33/569* (2006.01)
*C12Q 1/68* (2006.01)
*A61K 8/44* (2006.01)
*A61Q 11/00* (2006.01)
*C12Q 1/14* (2006.01)

(52) U.S. Cl.
CPC . *C12Q 1/689* (2013.01); *A61K 8/44* (2013.01); *A61Q 11/00* (2013.01); *C12Q 1/14* (2013.01); *G01N 33/56944* (2013.01); *G01N 2800/18* (2013.01)

(58) Field of Classification Search
None
See application file for complete search history.

(56) References Cited

U.S. PATENT DOCUMENTS

| 3,535,421 A | 10/1970 | Briner et al. |
|---|---|---|
| 3,538,230 A | 11/1970 | Morton et al. |
| 3,678,154 A | 7/1972 | Widder et al. |
| 3,696,191 A | 10/1972 | Weeks |
| 3,862,307 A | 1/1975 | Di Giulio |
| 3,925,543 A | 12/1975 | Donohue |
| 3,932,605 A | 1/1976 | Vit |
| 3,932,608 A | 1/1976 | Anderson et al. |
| 3,937,807 A | 2/1976 | Haefele |
| 3,943,241 A | 3/1976 | Anderson et al. |
| 3,959,458 A | 5/1976 | Agricola et al. |
| 3,988,434 A | 10/1976 | Schole et al. |
| 3,991,177 A | 11/1976 | Vidra et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,051,234 A | 9/1977 | Gieske et al. |
| 4,058,595 A | 11/1977 | Colodney |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,110,083 A | 8/1978 | Benedict |
| 4,146,607 A | 3/1979 | Ritchey |
| 4,154,813 A | 5/1979 | Kleinberg |
| 4,154,815 A | 5/1979 | Pader |
| 4,160,821 A | 7/1979 | Sipos |
| 4,213,961 A | 7/1980 | Curtis et al. |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| 4,340,583 A | 7/1982 | Wason |
| 4,355,022 A | 10/1982 | Rabussay |
| RE31,181 E | 3/1983 | Kleinberg et al. |
| 4,466,954 A | 8/1984 | Ichikawa et al. |
| 4,528,181 A | 7/1985 | Morton et al. |
| 4,532,124 A | 7/1985 | Pearce |
| 4,538,990 A | 9/1985 | Pashley |

(Continued)

FOREIGN PATENT DOCUMENTS

| CN | 1701518 | 11/2005 |
|---|---|---|
| EP | 0569666 | 11/1993 |

(Continued)

OTHER PUBLICATIONS

Kaufman. "A rapid enumeration method for salivary arginolytic (alkali-producing) bacteria". IADR/AADR/CADR 82nd General Session, Mar. 10-13, 2004, p. 1032A.*
Coogan et al. "Saliva and plaque acids in caries active and caries free subjects". Journal of the DASA, Dec. 1996, pp. 823-827.*
Machado et al. CaviStat Confection Inhibition of Caries in Posterior Teeth, Abstract, 83rd Session of the American Association for Dental Research, Mar. 21-24, 2007, New Orleans, LA.
Chatterjee et al,. Bacterial Acidification and CaviStat Alkalinization of Occlusal Fissure pH, Abstract, 83rd Session of the American Association for Dental Research, Mar. 9-12, 2005, Baltimore, MD.

(Continued)

*Primary Examiner* — Vera Afremova

(57) ABSTRACT

This, intention relates to methods of assessing the bioflora of the mouth and of providing appropriate treatment utilizing a basic amino acid in accordance with the assessment.

7 Claims, 2 Drawing Sheets

(56) References Cited

U.S. PATENT DOCUMENTS

| | | | |
|---|---|---|---|
| 4,645,662 A | 2/1987 | Nakashima et al. | |
| 4,656,031 A | 4/1987 | Lane et al. | |
| 4,725,576 A | 2/1988 | Pollock et al. | |
| 4,842,847 A | 6/1989 | Amjad | |
| 4,866,161 A | 9/1989 | Sikes et al. | |
| 4,885,155 A | 12/1989 | Parran, Jr. et al. | |
| 4,954,137 A | 9/1990 | Potter | |
| 4,976,951 A | 12/1990 | Rosenberg et al. | |
| 4,992,420 A | 2/1991 | Neeser | |
| 4,997,640 A | 3/1991 | Bird et al. | |
| 5,000,939 A | 3/1991 | Dring et al. | |
| 5,004,597 A | 4/1991 | Majeti et al. | |
| 5,032,386 A | 7/1991 | Gaffar et al. | |
| 5,043,154 A | 8/1991 | Gaffar et al. | |
| 5,096,700 A | 3/1992 | Siebel et al. | |
| 5,286,480 A | 2/1994 | Boggs et al. | |
| 5,334,617 A | 8/1994 | Ulrich et al. | |
| 5,370,865 A | 12/1994 | Yamagishi et al. | |
| 5,427,755 A | 6/1995 | Dany et al. | |
| 5,639,795 A | 6/1997 | Friedman et al. | |
| 5,747,004 A | 5/1998 | Giani et al. | |
| 5,762,911 A | 6/1998 | Kleinberg et al. | |
| 5,906,811 A | 5/1999 | Hersh | |
| 5,922,346 A | 7/1999 | Hersh | |
| 5,997,301 A | 12/1999 | Linden | |
| 6,217,851 B1* | 4/2001 | Kleinberg et al. | 424/49 |
| 6,436,370 B1 | 8/2002 | Kleinberg et al. | |
| 6,488,961 B1 | 12/2002 | Robinson et al. | |
| 6,524,558 B2 | 2/2003 | Kleinberg et al. | |
| 6,558,654 B2 | 5/2003 | McLaughlin | |
| 6,805,883 B2 | 10/2004 | Chevaus et al. | |
| 6,850,883 B1 | 2/2005 | Kapanen | |
| 7,056,541 B1* | 6/2006 | Stahl | 426/5 |
| 7,303,870 B2* | 12/2007 | Hunter et al. | 435/6.15 |
| 7,435,558 B2* | 10/2008 | Haberlein et al. | 435/25 |
| 2002/0064504 A1 | 5/2002 | Kleinberg et al. | |
| 2002/0081360 A1 | 6/2002 | Burgard et al. | |
| 2003/0124635 A1 | 7/2003 | Ukaji et al. | |
| 2004/0141960 A1 | 7/2004 | Hberlein et al. | |
| 2004/0185027 A1 | 9/2004 | Reierson et al. | |
| 2004/0258630 A1 | 12/2004 | Boyd et al. | |
| 2006/0127327 A1* | 6/2006 | Shi et al. | 424/50 |
| 2007/0154863 A1 | 7/2007 | Cai et al. | |

FOREIGN PATENT DOCUMENTS

| | | |
|---|---|---|
| JP | H07-258053 | 10/1995 |
| JP | H08-151324 | 6/1996 |
| JP | 2001-504083 | 3/2001 |
| JP | 2004-514169 | 5/2004 |
| JP | 2004-536574 | 12/2004 |
| JP | 2006-503089 | 1/2006 |
| RU | 2132182 | 6/1999 |
| RU | 2308036 | 10/2007 |
| WO | WO 97/32565 | 9/1997 |
| WO | WO 2007/011552 | 1/2007 |
| WO | WO 2007/068916 | 6/2007 |
| WO | WO 2009/099450 | 8/2009 |
| WO | WO 2009/099451 | 8/2009 |
| WO | WO 2009/099452 | 8/2009 |
| WO | WO 2009/099454 | 8/2009 |
| WO | WO 2009/099455 | 8/2009 |
| WO | WO2009100262 | 8/2009 |

OTHER PUBLICATIONS

Kleinberg I., A Mixed-Bacteria Ecological Approach to Understanding the Role of the Oral Bacteria in Dental Caries Causation: An Alternative to *Streptococcus* Mutans and the Specific-Plaque Hypothesis, CRIT. Rev. Oral Biol. Med,. 12(2): 108-125 (2002).

Kleinberg I., A New Salvia-Based Anticaries Composition, Dentistry Today, vol, 18, No. 2, Feb. 1999.

Acevedo et al., "The Inhibitory effect of an arginine bicarbonate/calcium carbonate (CaviStat)—containing dentifrice on the development of dental caries in Venezuelean school children", The Journal of clinical Dentistry, 2005, v.16, No. 3,pp. 63-70, ISSN 0895-8831.

Kaufman, 1032 A Rapid Enumeration Method for Salvary Arginolytic (Alkali-producing) Bacteria, The IADR/AADR/CADR 82nd General Session, Mar. 11, 2004 See the whole document.

Chin Lo-Hahn, Relationship between Caries Bacteria, Host Responses, and Clinical Signs and Symptons of Puliptis, JOE, vol. 33 No. 3., pp. 213-219, Mar. 3, 2007 See the whole document.

Abelson et al., 1986, "Modification of dental Plaque by arginine-urea to resist pH fall in vivo," Clinical Preventive Dentistry 8(1):7-10.

Edgar et al., 1982, "Effects of lysylarginine on plaque composition and metabolism in vivo," J. Dental Research 61(4):544, Abstract 78.

Grenier et al., 1973, "Identification of *Streptococcus* mutans serotypes in dental plaque by fluorescent antibody techniques," Archives of Oral Biology 18(6):707-715.

International Search Report and Written Opinion in International Application No. PCT/US2009/033287, mailed Sep. 15, 2009.

Moore et al., 1956, "The Formation of Lactic Acid in Dental Plaques I. Caries-Active Individuals," Journal of Dental Research 35(5):778-785.

Naini et al., 1989, "Plaque Ammonia Production in Caries-resistant (CR) and Caries-susceptible (CS) Adults,"J Dent Res 68:318 Abstract No. 1096.

Robinson et al., 1997, "A method for the quantitative site-specific study of the biochemistry within dental plaque biofilms formed in vivo," Caries Research 31(3):194-200.

Suzuki et al., 2005, "Quantitative analysis of multi-species oral biofilms by TaqMan Real-Time PCR," Clinical Medicine & Research 3(3):176-185.

Burne et al., 2000, "Alkali Production by Oral Bacteria and Protection against Dental Caries," FEMS Microbiol. Letters 193(1):1-6.

Bustin, 2002, "Quantification of mRNA Using Real-Time Reverse Transcription (RT-PCR): Trends and Problems," J. Molecular Endocrinology 29(1):23-39.

De Soet et al., 1990, "Monoclonal Antibodies for Enumeration and Identification of Mutans *Streptococci* in Epidemiological Studies," Arch. Oral Biol. 35(Supp.):165S-168S.

Federal Agency for Healthcare and Social Development, 2005, *A Method for Diagnosing and Treating the Oral Cavity Diseases Accompanied by Disorders of Microflora: A Handbook for Physicians*, The State Educational Setting of Supplementary Professional Education, The Russian Medical Academy of Postgraduate Education, Moscow, pp. 5-7.

Fedotov, 2007, Large Dictionary of Medical Terms, p. 340, Moscow.

Hoshino et al., 2004, "PCR Detection and Identification of Oral *Streptococci* in Saliva Samples Using gtf Genes," Diagn. Microbiol. Infect. Dis. 48(3):195-199.

Idone et al., 2003, "Effect of an Orphan Response Regulator on *Streptococcus* mutans Sucrose-Dependent Adherence and Cariogenesis,"Infect. Immun. 71(8):4351-4360.

International Search Report and Written Opinion in International Application No. PCT/US09/033287, mailed Sep. 15, 2009.

Keer et al., 2003, "Molecular Methods for the Assessment of Bacterial Viability," J. Microbiol. Methods 53(2):175-183.

Margolis, 1990, "An Assessment of Recent Advances in the Study of the Chemistry and Biochemistry of Dental Plaque Fluid," J. Dent. Res. 69(6):1337-1342.

Packaging with ingredient list for DenClude® (Launched Dec. 2004).

Packaging with ingredient list for ProClude® (Launched Jul. 2002).

Ryan et al., 1995, "A Comparative Study of Glucose and Galactose Uptake in Pure Cultures of Human Oral Bacteria, Salivary Sediment and Dental Plaque," Arch. Oral Biol.l 40(8):743-752.

Sheridan et al., 1998, "Detection of mRNA by Reverse Transcription-PCR as an Indicator of Viability in *Escherichia coli* Cells," Applied Environ. Microbiol. 64(4):1313-1318.

Shore et al., 2001, "Investigation to Evaluate and Validate the Leeds in situ Device for the Study of Enamel Remineralisation in vivo," J. Dent. 29(6):415-419.

Shu et al., 2007, "The Relationship between Dental Caries Status and Dental Plaque Urease Activity," Oral Microbiol. Immunol. 22(1):61-66.

(56) References Cited

OTHER PUBLICATIONS

Van Der Hoeven et al., 1985, "Effect of Utilization of Substrates on the Compositions of Dental Plaque," FEMS Microbiol. Letters 31(3):129-133.

Wijeyeweera et al., 1989, "Arginolytic and Ureolytic Activities of Pure Cultures of Human Oral Bacteria and Their Effects on the pH Response of Salivary Sediment and Dental Plaque in vitro," Arch. Oral Biol. 34(1):43-53.

US 5,989,525, 11/1999, Kleinberg et al. (withdrawn).

International Search Report and Written Opinion in International Application No. PCT/US08/058696, mailed Jan. 5, 2009.

Carlsson et al., "Establishment of Streptococcus sanguis in the mouths of infants," Archives of Oral Biology, Dec. 1970, 15(12):1143-1148.

Li et al., "Identification of Streptococcus sanguinis with a PCR-Generated Species-Specifi DNA Probe," Journal of Clinical Microbiology, Aug. 2003, 41(8):3481-3486.

\* cited by examiner

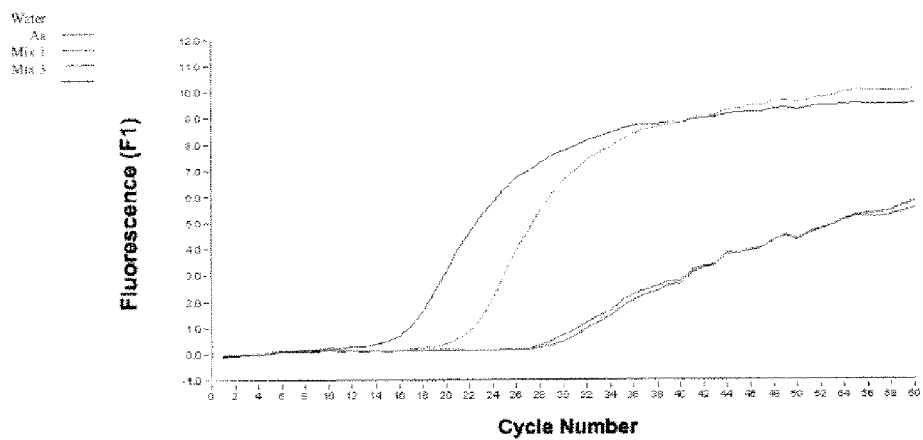
Figure 1. Amplification of *A. actinomycetemcomitans* from pure cultures and mixed species populations.
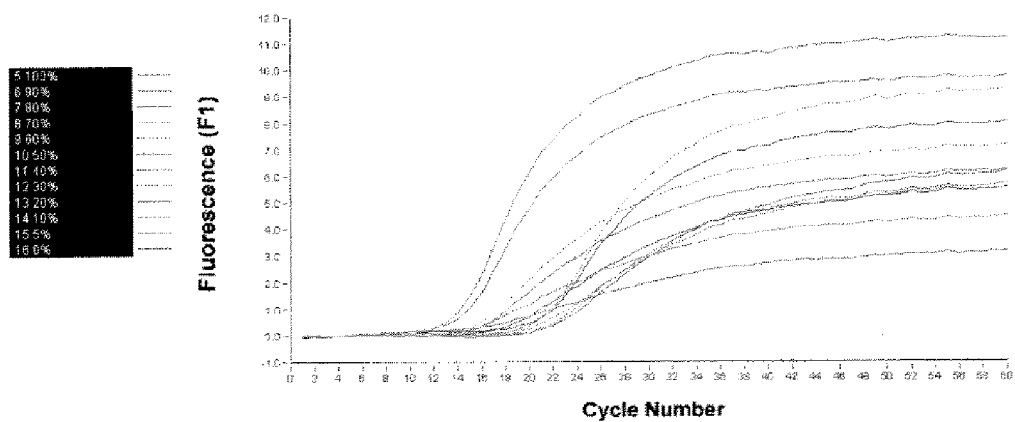
Figure 2. Amplification of RNA from mixes of live and dead *A. actinomycetemcomitans*.

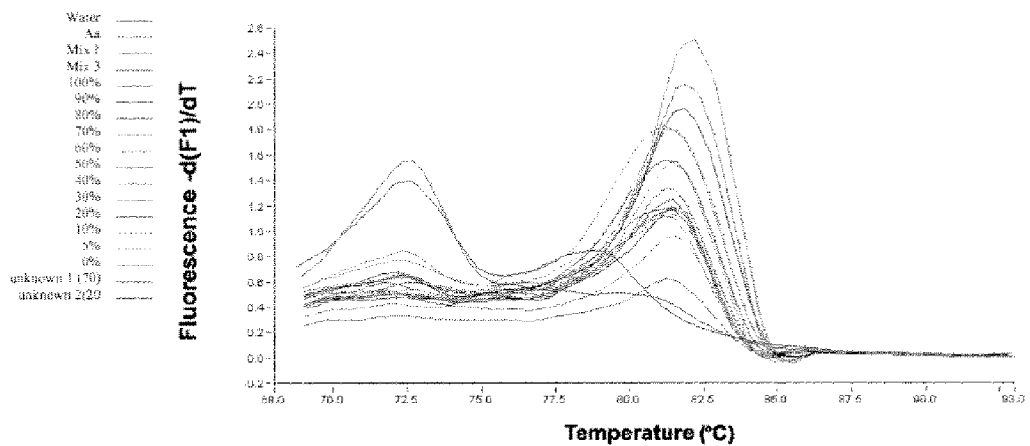
Figure 3. Melting peak analysis of products amplified from pure and mixed cultures of *A. actinomycetemcomitans*.
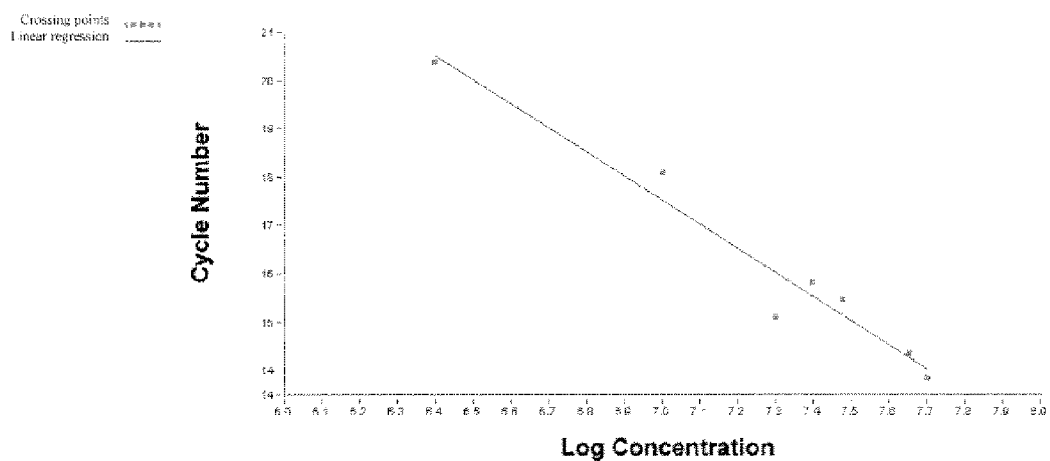
Figure 4. Standard curve and linear regression of the standard curve generated from the amplification of known concentrations of viable and dead *A. actinomycetemcomitans*.

ORAL CARE METHODS AND SYSTEMS

This application claims the benefit of U.S. patent application Ser. No. 61/027,437 filed Feb. 9, 2008, and also claims the benefit of U.S. patent application Ser. No. 61/027,442 filed Feb. 9, 2008, and U.S. patent application Ser. Nos. 61/027,432; 61/027,431; 61/027,420; and 61/027,435 all filed Feb. 8, 2008, the contents of which applications are all incorporated herein by reference.

FIELD OF THE INVENTION

This invention relates to methods of measuring relative levels of cariogenic and arginolytic bacteria in the mouth, e.g., as part of a dental care regimen using compositions comprising a basic amino acid in free or salt form.

BACKGROUND OF THE INVENTION

Arginine and other basic amino acids have been proposed for use in oral care and are believed to have significant benefits in combating cavity formation and tooth sensitivity. Commercially available arginine-based toothpastes are DenClude® and ProClude® containing CaviStat®, which contain arginine and calcium bicarbonate.

The type of bioflora in the mouth plays a significant role in the development of cavities and in oral health generally. For example, it has been hypothesized that a significant factor in the beneficial effect of arginine is that arginine and other basic amino acids can be metabolized by certain types of bacteria, e.g., *S. sanguis* which are not cariogenic and which compete with cariogenic bacteria such as *S. mutans*, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities It would be useful to have an efficient way to monitor the type of bioflora in the mouth, e.g., to determine the optimal treatment and to monitor the effectiveness of treatment of patients.

BRIEF SUMMARY OF THE INVENTION

The invention provides quick and simple methods for assessing the bioflora in the mouth.

In a first embodiment, the invention measures plaque ammonia production levels to determine the relative population of arginolytic bacteria.

In another embodiment, the invention measures plaque lactic acid levels to determine the relative population of cariogenic bacteria.

In another embodiment, the invention uses the polymerase chain reaction (PCR), for example quantitative real time PCR, to characterize the bioflora in the mouth, e.g., in the plaque or saliva.

In another example, the invention uses reverse transcriptase PCR (RT-PCR) to characterize the bioflora in the mouth, e.g., in the plaque or saliva.

In another embodiment, antibody probes, e.g., fluorescent antibody probes are used to characterize the bioflora in the mouth, e.g., in the plaque or saliva.

For example, the invention quantifies levels of at least one cariogenic bacteria, e.g., *S. mutans*, and at least one arginolytic bacteria, e.g., *S. sanguis*.

In another embodiment, the patient is assessed using one of the foregoing methods, and treatment prescribed accordingly.

The methods of the invention are particularly useful to detect potentially damaging changes in plaque ecology and to allow corrective treatment before there is measurable or significant demineralization or damage to the teeth.

The invention thus provides methods to enhance oral health, e.g., to
 a. reduce or inhibit formation of dental caries,
 b. reduce or inhibit demineralization and promote remineralization of the teeth,
 c. treat, reduce or inhibit formation of early enamel lesions,
 d. reduce hypersensitivity of the teeth,
 e. reduce or inhibit gingivitis,
 f. promote healing of sores or cuts in the mouth,
 g. reduce levels of acid producing bacteria,
 h. increase relative levels of arginolytic bacteria,
 i. inhibit microbial biofilm formation in the oral cavity,
 j. raise and/or maintain plaque pH at levels of at least pH 5.5 following sugar challenge,
 k. reduce plaque accumulation,
 l. treat, relieve or reduce dry mouth,
 m. whiten teeth,
 n. enhance systemic health, including cardiovascular health, e.g., by reducing potential for systemic infection via the oral tissues,
 o. immunize the teeth against cariogenic bacteria and their effects,
 p. clean the teeth and oral cavity and/or
 q. reduce erosion of the teeth
comprising measuring the bioflora of the oral cavity, e.g., using any of the foregoing methods, and if indicated, administering an oral care product comprising an effective amount of a basic amino acid or salt thereof, e.g., arginine.

The invention further provides the use of a basic amino acid, in free or salt form, for the manufacture of medicament for enhancing oral health in a subject whose oral cavity bioflora comprise elevated levels of cariogenic bacteria and/or elevated lactate levels, and/or low levels of arginolytic bacteria and/or low levels of plaque ammonia production, as measured by a method according to the present invention.

The invention further provides a method for cosmetically enhancing the oral cavity (wherein such cosmetic enhancement may include e.g. making teeth whiter and/or reducing halitosis) which method comprises measuring the bioflora of the oral cavity using a method according to the present invention, and if indicated by the presence of elevated levels of cariogenic bacteria and/or elevated lactate levels, and/or the presence of low levels of arginolytic bacteria and/or low levels of plaque ammonia production, administering an oral care product comprising a basic amino acid in free or salt form.

BRIEF DESCRIPTION OF THE DRAWINGS

FIG. 1 depicts the amplification of *A. actinomycctemcomitans* from pure cultures and mixed species populations.
FIG. 2 depicts the amplification of RNA from mixes of live and dead *A. actinomycetemcomitans*.
FIG. 3 depicts melting peak analysis of products amplified from pure and mixed cultures of *A. actinomycetemcomitans*.
FIG. 4 is the standard curve and linear regression of the standard curve generated from the amplification of known concentrations of viable and dead *A. actinomycetemcomitans*.

DETAILED DESCRIPTION

Plaque Metabolism-Ammonia Production

The ability of dental plaque to convert arginine to ammonia is a marker of arginolytic activity. Certain bacteria have the ability to convert arginine to ammonia, just as certain bacteria can convert sugars to acid. It is beneficial to increase the relative concentration of arginolytic species because these bacteria create conditions that are unfavorable for proliferation of cariogenic bacteria, which favor acidic conditions and increase caries risk. Daily use of arginine is expected to create a shift in the plaque ecology that favors arginolytic bacteria in an analogous manner that frequent consumption of sugar creates conditions that favor acid producing bacteria. Ammonia is a base that is capable of neutralizing acids and helps maintain neutral plaque pH. Neutral pH conditions are more favorable to nonpathogenic bacteria. Measurement of ammonia production measures the contribution from all the bacteria capable of converting arginine to ammonia. This is in contrast to the real time PCR method (further described below) which measures concentration of select arginolytic bacteria and does not distinguish between metabolically active (live) and inactive (dead) bacteria.

Ammonia detection kits are available commercially, e.g., from Diagnostic Chemicals Limited (Oxford, Conn.) to measure ammonia production. The principle for the quantification and determination is that ammonia is known to react with alpha-ketoglutarate and reduced nicotinamide adenine dinucleotide phosphate (NADPH) to form L-glutamate and NADP. The reaction is catalyzed by glutamate dehydrogenase (GLDH). The decrease in absorbance at 340 nm due to the oxidation of NADPH is proportional to the ammonia concentration. Plaque samples are collected after a pre-defined treatment protocol. In some applications, plaque is harvested from enamel or HAP specimens mounted on a retainer. In other applications, plaque is harvested directly from the teeth.

Plaque Ecology by Lactic Acid Levels

Just as the measurement of ammonia levels serves as a proxy to measure the levels of arginolytic bacteria, lactic acid serves as a proxy to measure the levels of cariogenic bacteria. Subjects have plaque taken without morning oral hygiene and without eating or drinking from the previous evening. They rinse with a 10% sucrose solution for 2 minutes. After 8 minutes, plaque is collected by scraping the tooth surface(s). Plaque samples are collected on ice in preweighed tubes, and the plaque weight is determined. The analysis includes adding ice cold water to the known amount of plaque samples then heating the samples to 80 deg C. for 5 minutes to kill the bacteria and to release all acids before the samples are cooled in ice water for an additional 5 minutes. The samples are then centrifuged and the supernatant is filtered. The lactate concentration is measured using Capillary Electrophoresis.

Plaque Ecology by Quantitative Real Time PCR

Quantitative real time PCR (Polymerase Chain Reaction) is a highly sensitive means of quantifying DNA. Bacterial DNA isolated from dental plaque is used to quantify the total levels of bacteria since the amount of DNA is directly related to the amount bacteria present. Real time PCR is recognized by government organizations such as the Center for Disease Control and the FDA as a very powerful and sensitive technique. Faking advantage of the known genomic sequence of many oral bacteria, probes are designed to detect total levels of oral bacteria or specific bacteria such as S. mutans or S. sanguis. DNA isolated from the samples of plaque or saliva is amplified by the polymerase chain reaction. The amount of DNA increases exponentially with each cycle of the PCR reaction. The technique is referred to as "real time" because the reaction is followed in real time through the use of fluorescent report molecules. In one embodiment of the invention, SYBR Green is used as the reporting molecule. This molecule fluoresces strongly upon coordination with double stranded DNA. Quantification is achieved by setting a fluorescent threshold and using DNA standards at various concentrations to determine the number of cycles needed to reach the threshold. The more DNA present, the smaller number of DNA cycles are needed to reach the threshold. Commercial Real Time PCR instruments are available from numerous manufacturers, such as Roche Diagnostics.

Plaque samples are harvested from enamel or hydroxyapatite specimens with known and constant surface area. Standardization of plaque collection is critical because the amount of DNA present is directly related to how much plaque is collected. It is inappropriate to use plaque mass as a means standardizing total bacteria measured by real time PCR because the two quantities are significantly correlated. The results reported as µg DNA per ml. Statistics can be performed on the DNA concentration or Ln(DNA concentration). For total bacteria, a two factor ANOVA is performed using the subject and treatment as factors. Differences are considered significant if a difference is detected a 95% confidence level. For specific bacteria such as S. mutans or S. sanguis, a two factor ANCOVA is conducted using the total bacteria as the covariate. The total amount of specific bacteria as it relates to the total bacterial population is a more relevant marker of plaque ecology health.

In a particular embodiment of the invention, S. mutans is measured as a marker for cariogenicity S. mutans is chosen because it is a well accepted risk factor associated in the initiation of dental caries. While other acid producing bacteria are involved in the caries process, S. mutans is known to play a significant role particularly in the initiation and early stages of the cariogenic process. In one embodiment of the invention, S. sanguis is chosen as a marker for a shift to healthier plaque ecology because S. sanguis is a bacteria known to exhibit a high level of arginolytic activity (ability to convert arginine to ammonia).

Plaque ecology by RT-PCR

Reverse transcription PCR measures RNA transcripts in a sample. The RNA is isolated, the transcripts converted to cDNA using reverse transcriptase, and the cDNA is amplified using PCR. The advantage of RT-PCR is that DNA-based methods for the detection of oral bacteria are unable to determine the viability of those species. Because oral bacteria are most often found in biofilm communities, the DNA of dead bacteria can be retained within the biofilm architecture for long periods of time following killing. Other methods, such as fluorescence-based viability assays (Live Dead kit, Molecular Probes), can detect whether or not organisms have compromised membranes, but do not directly detect specific species.

Reverse transcription real time PCR is thus a method to quantify the viable organisms of a specific species of oral bacteria present within in a complex community. mRNA has a relatively short half life and therefore is indicative of recently active bacteria. We have developed species-specific primers to the elongation factor tuf. This gene is not significantly regulated by growth phase, media or environmental conditions, thereby minimizing spurious effects on detected numbers of bacteria. Using *Aggregatibacter actinomycetemcomitans* as our test organism, viability differences in mixed populations of live and EtOH killed bacteria may be detected when as few as 20% of the organisms present are viable. Additionally, the method allows reliable identification of the presence of *A. actinomycetemcomitans* in mixed species populations containing up to six different species of bacteria. Calculated bacterial concentrations correlated closely to values estimated based on $OD_{610}$ for the same cultures (r=0.96, <1% difference). This assay represents a means of studying the ecology of specific organisms within the complex environment of the oral cavity. As further genetic sequence data becomes available, primers can be developed to a wide variety of oral bacteria.

Bacterial Levels by Fluorescent Antibody Probe

A caries diagnostic kit is used to detect the level of a cariogenic type of bacteria, e.g., *S. mutans* and/or for a non-cariogenic type, e.g., *S. sanguis*, in saliva through the use of monoclonal antibodies. The particular antibodies used are specific for the species of bacteria and have a fluorescent dye attached to the antibody. The levels of bacteria can be detected by measuring the amount of fluorescence that is emitted.

EXAMPLES

Example 1

Real Time PCR to Measure Total Plaque Bacteria Levels

Levels of total plaque bacteria (micrograms bacterial DNA/ml) in subjects is measured using different toothpaste formulations, using the procedures described supra:

|  | Total bacterial DNA | *S. mutans* DNA | *S. sanguis* DNA |
|---|---|---|---|
| 250 ppm fluoride formulation (control) | 6.091 | 0.09622 | 1.126 |
| 1450 ppm fluoride formulation | 6.018 | 0.09903 | 1.107 |
| Formulation having 2% arginine bicarbonate and 1450 ppm fluoride | 3.781 | 0.05998 | 1.291 |

The arginine-fluoride formulation is effective to reduce total bacterial plaque loads, and *S. mutans* (cariogenic) plaque loads, while enhancing *S. sanguis* (arginolytic) loads.

Example 2

Ammonia Production

Ammonia production is measured in subjects using different toothpaste formulations, using the method described above:

|  | Ammonia level (ppm) |
|---|---|
| 250 ppm fluoride formulation (control) | 1.97 |
| 1450 ppm fluoride formulation | 1.79 |
| Formulation having 2% arginine bicarbonate and 1450 ppm fluoride | 2.77 |

Ammonia production is significantly higher in plaque of subjects using the arginine-containing formulation.

Example 3

Lactic Acid Levels

Plaque lactic acid levels are measured in subjects using capillary electrophoresis as described above, showing that lactate is significantly increased in the presence of sucrose.

|  | Plaque | Sucrose Challenged Plaque |
|---|---|---|
| Lactate (nmol/mg) | 1.87 | 7.82 ± 0.37 |

Example 4

Real Time PCR/RT-PCR

This invention combines the principles of real-time PCR detection of bacterial species with the use of messenger RNA (mRNA) as an indicator of biological activity within cells. Following purification of mRNA from a bacterial sample, reverse transcription real time PCR is used to detect and quantify specific bacteria within a simple or complex environment. The invention covers the sequence of the primers as well as the mRNA identification method and its application.

One function of DNA within viable cells is to code for the synthesis of proteins. DNA codes for its corresponding mRNA strand which is then used as the instructions for assembling finished proteins. Unlike DNA, mRNA has a very short half life (seconds to minutes) and is only present in cells that are either viable or very recently killed. Whereas DNA is present in cells in a fixed number of copies, mRNA levels are often changed in response to the conditions in which a cell exists. Expression of different proteins may be up-or down-regulated in response to temperature changes, growth media, growth phases and other environmental conditions. Therefore, if the target gene is not carefully chosen, it is possible that fluctuations in environmental conditions will be falsely read as fluctuations in population viability. To avoid these effects, the present invention uses elongation factor tu, the gene tuf, as the target sequence. This sequence has previously been used as a marker because little or no alteration in tuf expression has been observed under different experimental conditions.

Real time PCR uses the basic chemistry behind polymerase chain reaction (PCR) amplification of genetic material and couples it with real time detection of fluorescent labels as a mechanism of quantifying the number of copies of a given genetic sequence present after each amplification cycle. The simplest of these methods uses SYBR Green I, a fluorescent probe that intercalates specifically into double stranded DNA (dsDNA). Increasing levels of SYBR Green fluorescence therefore correlate to greater concentrations of dsDNA. When this dye is included in a PCR reaction primed using specific genetic sequences, the increase in fluorescence corresponds to an increase in the number of copies of the target gene. Subsequently, the cycle number at which the signal crosses a predetermined intensity threshold can be correlated to the concentration of the genetic sequence in the starting material.

The development of real time PCR technology has made it possible to detect and quantify specific biological species rapidly and with a high degree of accuracy. Conventional methods for quantification of bacterial species rely on the development of primers to the variable region of the DNA encoding the 16s ribosomal subunit. This subunit is critical to bacterial replication and its sequence is, therefore, not readily mutated. The detection of 16s rDNA sequences specific to a particular species can facilitate the detection and enumeration of a single bacterial species within a complex environment.

Primers are designed based on the sequences of tuf genes from publically available databases (National Center for Biotechnology Information and the Los Alamos Oral Pathogens Database). Sequences are aligned using the DNA Star Lasergene program MegAlign module. This alignment is used to select a region of greater divergence in order to maximize the likelihood of species specificity. Primer sequences are selected based upon analysis information available from the Roche Diagnostics LightCycler Probe Design software. Primers covered by this invention include not only those already designed and tested, but all primers to this genetic region in oral pathogens.

Total RNA is isolated from samples using an appropriate RNA isolation kit or other RNA isolation method. Any preferred method for RNA isolation can be used. Purified RNA is treated 2 times with appropriate DNase treatment reagents. This step degrades any contaminating DNA within the RNA prep and prevents the acquisition of false positives. Isolated RNA is then reverse transcribed to generate a complimentary DNA (cDNA) molecule. The resulting cDNA is amplified and detected using SYBR Green. As a quality control for the complete removal of DNA, a real time PCR reaction can be run without the reverse transcription step. PCR products obtained in the absence of a reverse transcription reaction must be the result of contaminating DNA.

A standard curve is generated by performing the real time reverse transcription PCR reaction on RNA samples isolated from cultures containing known amounts of viable bacteria. The second derivative maximum value for each known sample is plotted against its known concentration of bacterial cells. The second derivative maximum of amplification curves of RNA isolated from unknown bacterial samples can then be compared to the standard curve to determine the concentration of viable organisms within the sample population. This data would be valuable information in deterring the effects of antibacterials and active molecules on the ecology of the oral environment.

The following primer pair is designed to amplify a 228 base pair region of the tuf gene from *Aggregatibacter* (*Actinobacillus*) *actinomycetemcomitans*:

therefore be negative for amplification with these primers. "Mix 3" is from a population containing *A. actinomycetemcomitans, Porphyromonas gingivalis, Streptococcus gordonii, Streptococcus mutatis*, and *Streptococcus sanquinis* and should be positive for amplification of *A. actinomycetemcomitans*.

This graph demonstrates that while the mix containing *A. actinomycetemcomitans* is amplified with a similar curve to the positive control, the mix lacking it follows the same amplification curve as the water control, indicating that these primers are able to accurately detect *A. actinomycetemcomitans* from within a mix of RNA species.

The ability of these primers to accurately detect and quantify only viable *A. actinomycetemcomitans* organisms is determined as follows. A known concentration of *A. actinomycetemcomitans* cells are killed by suspending in 80% ethanol for 15 minutes. The bacteria are then pelleted by centrifugation and resuspended in fresh Brain Heart Infusion broth growth media. The ethanol killed bacteria are incubated overnight at 37° C. and examined for growth to confirm that no viable organisms were remained. The ethanol killed bacteria are then mixed, in defined ratios, with viable organisms and reverse transcription followed by real time PCR is performed. The amplification of these samples is shown in FIG. 2, which shows the amplification of RNA from mixes of live and dead *A. actinomycetemcomitans*.

Despite the fact that all of the populations used as templates for this reaction contained the same total number of organisms, earlier amplification is observed in samples containing more viable organisms, indicating that this assay is able to detect viable organisms within a mix of both live and dead bacteria. Additionally, the melting curve of these samples, as shown in FIG. 3, indicates that a single, identical product is amplified in all samples, which demonstrates the high specificity of the assay. FIG. 3 shows a melting peak analysis of products amplified from pure and mixed cultures of *A. actinomycetemcomitans*. The overlap of these curves indicates that a single product is being amplified from all samples. Table 2 shows a comparison of expected and calculated number of organisms in selected standard curve samples.

TABLE 1

| Primer name | Sequence | Tm (° C.) | % GC | ΔG (kcal/mol) | Annealing Temp. |
|---|---|---|---|---|---|
| Forward | 5' - AAGCGCGTGGTATCAC - 3' | 49.05 | 56.25 | −27.56 | 55° C. |
| Reverse | 5' - TGTAAGGAACACCTA - 3' | 31.52 | 40.00 | −20.15 | 55° C. |

Properties of primers designed for quantification of mRNA expression of tuf in *A. actinomyeetemcomitans*.

These primers are used to amplify RNA isolated from both pure cultures of *A. actinmoycetemcomitans* and mixed populations both with and without *A. actinomycetemcomitans* included. The results, in particular the relationship between fluorescence (Fl) and cycle number are shown in the graph of FIG. 1. In FIG. 1, "water" represents the negative control and "Aa" is the positive control of pure *A. actinomycetemcomitans* culture. "Mix 1" was purified from a population containing *Prevoltella intermedia, Streptococcus sobrinus, Streptococcus oralis*, and *Actinomyces viscosus* and should,

TABLE 2

Comparison of expected and calculated number of organisms in selected standard curve samples.

| Sample | Expected viable CFU | Calculated viable CFU |
|---|---|---|
| 100% | $5.00 \times 10^7$ | $5.34 \times 10^7$ |
| 50% | $2.50 \times 10^7$ | $2.28 \times 10^7$ |
| 40% | $2.00 \times 10^7$ | $2.54 \times 10^7$ |

TABLE 2-continued

Comparison of expected and calculated number of organisms in selected standard curve samples.

| Sample | Expected viable CFU | Calculated viable CFU |
|---|---|---|
| 30% | $1.50 \times 10^7$ | $1.18 \times 10^7$ |
| 20% | $1.00 \times 10^7$ | $1.07 \times 10^7$ |
| 10% | $5.00 \times 10^6$ | $4.06 \times 10^6$ |
| 5% | $2.50 \times 10^6$ | $2.96 \times 10^6$ |

Based on the known concentrations of the viable and killed starting cultures, the approximate number of viable organisms in each population is calculated and used in conjunction with the second derivative maximum of each amplification curve to generate a standard curve. The results are shown in FIG. 4, which illustrates a standard curve and linear regression of the standard curve generated from the amplification of known concentrations of viable and dead *A. actinomycetemcomitans*. The $r^2$ value of the regression line is 0.96.

The $r^2$ value of a linear regression line indicates the closeness of fit of the regression equation to the observed values. An $r^2$ closer to 1.00 indicates that the observed values match closely to the regression line. For the example above, the $r^2$ value of the standard curve is 0.96, indicating that about 96% of the total variation observed in the line is due to actual measured variation in the samples and that this standard curve can be used to calculate the concentration of viable organisms in unknown populations.

In practice, in a single experiment, the concentration of viable organisms calculated based on this standard curve is not significantly different from the actual concentration added prior to RNA isolation and differed by <20%. These data indicate that this assay represents a rapid, accurate means of detecting and quantifying viable organisms of a specific species within a complex population of organisms. This represents a potentially powerful tool for analyzing the effects of treatments on oral microbial ecology.

measuring levels of the arginolytic bacteria *S. sanguis* and the cariogenic bacteria *S. mutans* present in the sample of plaque using quantitative real time PCR and quantitative RT-PCR, wherein the quantitative real time PCR detects and quantifies the amounts of the variable domains of the 16S ribosomal subunit DNA from each of the *S. sanguis* and the *S. mutans*; and wherein the quantitative RT-PCR detects mRNA levels produced by a gene from each of the *S. sanguis* and the *S. mutans*, wherein the expression of such gene does not fluctuate in response to environmental conditions and wherein the level of mRNA for each such gene correlates with the viability of the *S. sanguis* and the *S. mutans* respectively; and administering an oral care composition to the oral cavity of the patient for a treatment period sufficient to increase the levels of arginolytic bacteria and reduce the levels of cariogenic bacteria present in the oral cavity of the patient;

wherein the oral care composition comprises arginine or a salt thereof.

2. The method of claim 1, wherein the oral care composition further comprises a fluoride ion source.

3. The method of claim 2 wherein the fluoride ion source is selected from stannous fluoride, sodium fluoride, potassium fluoride, sodium monofluorophosphate, sodium fluorosilicate, ammonium fluorosilicate, amine fluoride, ammonium fluoride, and combinations thereof.

4. The method of claim 1, wherein the oral care composition further comprises a potassium ion source.

5. The method of claim 4, wherein the potassium ion source is selected from potassium nitrate and potassium chloride.

The invention claimed is:

1. A method to assess the bioflora of the oral cavity of a patient in order to determine an oral care treatment for the patient comprising:

obtaining a sample of plaque from the oral cavity of the patient;

6. The method of claim 2, wherein the oral care composition further comprises a potassium ion source.

7. The method of claim 3, wherein the oral care composition further comprises a potassium ion source selected from the group consisting of potassium nitrate and potassium chloride.

* * * * *

SEQUENCE LISTING

```
<160> NUMBER OF SEQ ID NOS: 2

<210> SEQ ID NO 1
<211> LENGTH: 16
<212> TYPE: DNA
<213> ORGANISM: Rattus norvegicus

<400> SEQUENCE: 1
aagcgcgtgg tatcac                                                      16

<210> SEQ ID NO 2
<211> LENGTH: 15
<212> TYPE: DNA
<213> ORGANISM: Rattus norvegicus

<400> SEQUENCE: 2
tgtaaggaac accta                                                       15
```